US008845631B2

(12) United States Patent
Werneth et al.

(10) Patent No.: US 8,845,631 B2
(45) Date of Patent: Sep. 30, 2014

(54) SYSTEMS AND METHODS OF PERFORMING MEDICAL PROCEDURES

(75) Inventors: Randell L. Werneth, San Diego, CA (US); Marshall Sherman, Cardiff by the Sea, CA (US); Mark T. Stewart, Lino Lakes, MN (US); J. Christopher Flaherty, Topsfield, MA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 745 days.

(21) Appl. No.: 12/769,350

(22) Filed: Apr. 28, 2010

(65) Prior Publication Data

US 2011/0270237 A1   Nov. 3, 2011

(51) Int. Cl.
| | |
|---|---|
| *A61B 18/12* | (2006.01) |
| *A61B 5/06* | (2006.01) |
| *A61B 5/053* | (2006.01) |
| *A61B 18/00* | (2006.01) |
| *A61B 5/00* | (2006.01) |
| *A61B 19/00* | (2006.01) |
| *A61B 5/01* | (2006.01) |
| *A61B 5/08* | (2006.01) |
| *A61B 18/24* | (2006.01) |
| *A61B 18/02* | (2006.01) |
| *A61B 18/14* | (2006.01) |
| *A61B 5/103* | (2006.01) |
| *A61B 5/0402* | (2006.01) |

(52) U.S. Cl.
CPC ....... *A61B 5/053* (2013.01); *A61B 2018/00791* (2013.01); *A61B 5/7207* (2013.01); *A61B 5/063* (2013.01); *A61B 5/06* (2013.01); *A61B 2018/00875* (2013.01); *A61B 5/0538* (2013.01); *A61B 2019/5246* (2013.01); *A61B 2019/465* (2013.01); *A61B 5/01* (2013.01); *A61B 5/08* (2013.01); *A61B 18/24* (2013.01); *A61B 18/0206* (2013.01); *A61B 2018/0262* (2013.01); *A61B 5/743* (2013.01); *A61B 18/1492* (2013.01); *A61B 5/103* (2013.01); *A61B 5/6885* (2013.01); *A61B 5/0402* (2013.01)
USPC ........................................................ 606/34

(58) Field of Classification Search
USPC ............ 606/32, 38, 34; 607/98, 99, 115, 119, 607/154; 600/374, 393
See application file for complete search history.

(56) References Cited

U.S. PATENT DOCUMENTS 5,335,668 A   8/1994   Nardella
5,536,267 A   7/1996   Edwards et al.

(Continued)

FOREIGN PATENT DOCUMENTS

| CN | 101208045 A | 6/2008 |
| CN | 101347331 A | 1/2009 |
| CN | 101505672 A | 8/2009 |
| EP | 1757227 A2 | 2/2007 |

*Primary Examiner* — Michael Peffley
*Assistant Examiner* — Thomas Giuliani
(74) *Attorney, Agent, or Firm* — Christopher & Weisberg, P.A.

(57) ABSTRACT

A medical method is provided, including a medical device having a distal assembly including at least one electrode and at least one treatment element, the medical device generating information regarding at least one of a physiological measurement and an operational parameter of the medical device; a plurality of surface electrodes affixable to a skin of the patient, wherein the surface electrodes are in electrical communication with the distal assembly to obtain position information of the medical device; and a processor pairing the position information and the at least one of a physiological measurement and an operational parameter of the medical device.

5 Claims, 9 Drawing Sheets

(56) References Cited

U.S. PATENT DOCUMENTS

| | | | |
|---|---|---|---|
| 5,697,377 A | 12/1997 | Wittkampf | |
| 5,718,701 A | 2/1998 | Shai et al. | |
| 5,983,126 A | 11/1999 | Wittkampf | |
| 6,546,935 B2 | 4/2003 | Hooven | |
| 6,714,806 B2 | 3/2004 | Iaizzo et al. | |
| 6,743,225 B2 | 6/2004 | Sanchez et al. | |
| 6,752,765 B1 | 6/2004 | Jensen et al. | |
| 7,599,730 B2 | 10/2009 | Hunter et al. | |
| 7,756,576 B2 * | 7/2010 | Levin | 600/547 |
| 2003/0199938 A1 | 10/2003 | Smits et al. | |
| 2004/0133113 A1 | 7/2004 | Krishnan | |
| 2004/0254437 A1 * | 12/2004 | Hauck et al. | 600/374 |
| 2007/0255162 A1 | 11/2007 | Abboud et al. | |
| 2008/0065061 A1 | 3/2008 | Viswanathan | |
| 2009/0264739 A1 * | 10/2009 | Markowitz et al. | 600/424 |

* cited by examiner

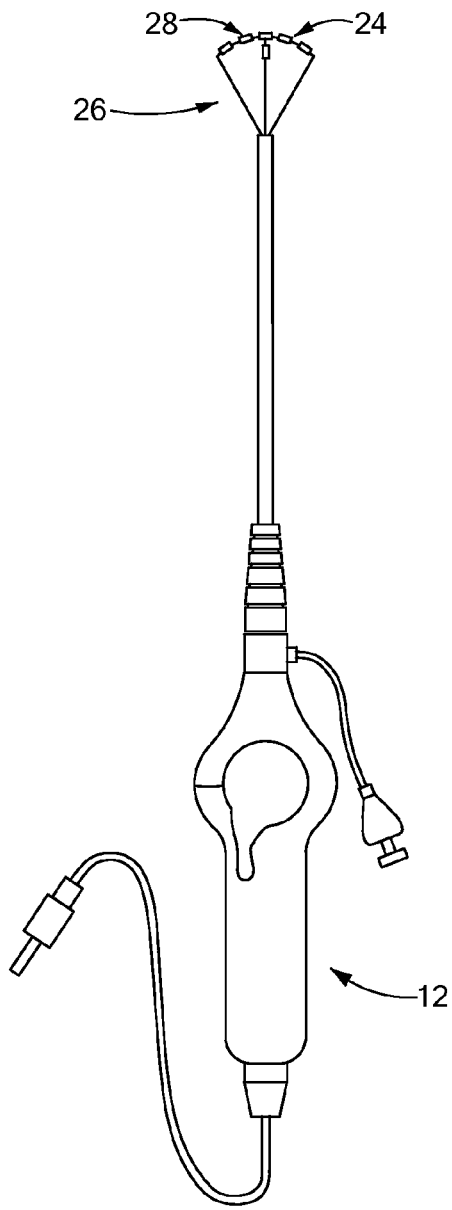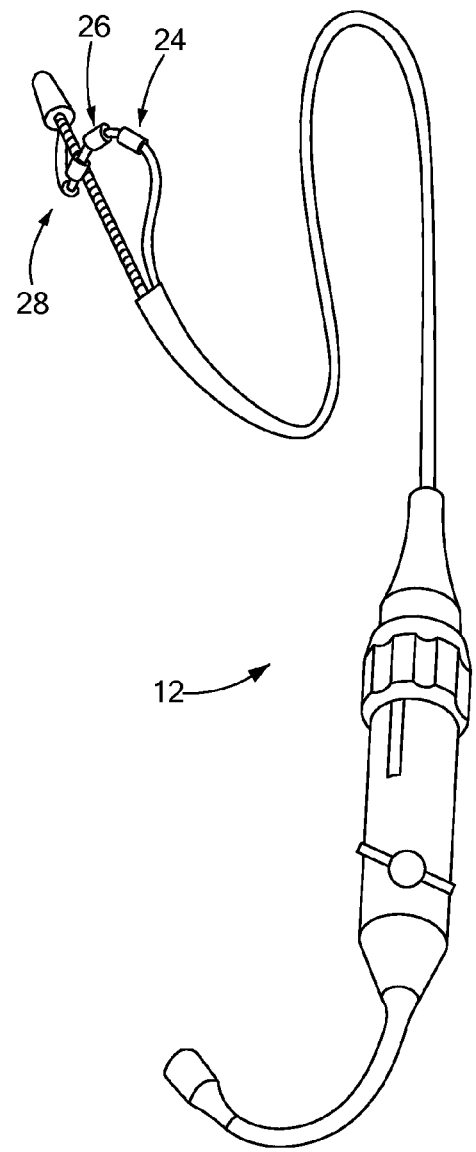
*FIG. 6*
*FIG. 7*

SYSTEMS AND METHODS OF PERFORMING MEDICAL PROCEDURES

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for pairing multi-dimensional position information with device-measured treatment information during a medical procedure.

BACKGROUND OF THE INVENTION

Medical procedures used to treat a variety of cardiovascular maladies, such as a trial fibrillation, typically involve the use of catheters having multiple sensors, electrodes, cryogenic chambers, or other measurement and treatment components to treat the diseased area of the heart or vasculature. Typically, such minimally invasive and intravascular devices are routed through a femoral artery or other passageway into the heart under guided fluoroscopy or other imaging techniques. For example, monoplane or biplane fluoroscopic imaging can be used estimate the position of the catheter within the heart. Another method to determine position information for an inserted medical device during cardiac procedures is to measure the opposition to time-varying electric current in an electric circuit, or impedance, provided by the tissue surrounding the target tissue. This is typically achieved by placing one or more impedance sensors or electrodes on or in the patient's body and measuring the impedance or electric potential between one of the sensors or electrodes and an electrode or sensor on the catheter.

In addition to the use of imaging to monitor or guide the position of a medical device within a patient, there are often numerous other informational parameters provided, monitored, and/or recorded both with respect to both the patient and the actual medical device. For example, during a therapeutic application such as cardiac or other tissue ablation, measurements may be taken by the medical device as to tissue temperature, electrical activity of the tissue, various impedance measurements of the tissue and/or surrounding environment. In addition, parameters such as pressure, structural integrity (e.g. leak presence), diameter of a device (where balloons may be included, for example), fluid flow rate, etc. may be taken with respect to the device itself. Such device-originated information may be provided on a control panel, status monitor or other display unit or device within the treatment/operating room.

Given the often numerous, independent sources of information regarding a particular procedure presented to a physician during treatment, it may prove difficult to keep track of the various parameters regarding device positioning, operation, and the efficacy of the delivered treatment. In view of the above, it is desirable to provide systems and methods of use thereof for pairing positional information of a medical device within a patient with device-based operational or physiological information for use during a medical procedure.

SUMMARY OF THE INVENTION

The present invention advantageously provides medical methods and systems for performing a medical procedure. In particular, a medical system is provided including a medical device having a distal assembly including at least one electrode and at least one treatment element, the medical device generating information regarding at least one of a physiological measurement and an operational parameter of the medical device; a plurality of surface electrodes affixable to a skin of the patient, where the surface electrodes are in electrical communication with the distal assembly to obtain position information of the medical device; a processor pairing the position information and the at least one of a physiological measurement and an operational parameter of the medical device. A reference electrode may be affixable to the skin of patient, the reference electrode being in electrical communication with the distal assembly, and the treatment element may include a radiofrequency ablation element or a cryogenic ablation element. The plurality of electrodes may include at least three pairs of surface electrodes that cooperate with the distal assembly to measure electric potential in three different planes. The physiological measurement may include a measured tissue impedance, and the position information and the at least one of a physiological measurement and an operational parameter of the medical device may be obtained sequentially or simultaneously.

A medical method is also provided, including inserting a medical device into the body of a patient; obtaining position information of the medical device; treating a tissue site with the medical device; obtaining at least one of a physiological measurement of the tissue site and an operational parameter of the medical device; pairing the position information with the at least one of a physiological measurement of the tissue site and an operational parameter of the medical device; and modifying the treatment of the tissue site based at least in part on the paired information. Modifying the treatment may include terminating the treatment. The method may include graphically displaying the paired information.

Another medical method is provided, including applying at least three pairs of surface electrodes to the skin of a patient; applying an electric potential between each of the at least three electrode pairs; providing a medical device having a distal assembly with at least one electrode and at least one ablation element; inserting the medical device into the body of the patient; obtaining three-dimensional position information of the medical device; ablating tissue at a tissue site with the ablation element; measuring an impedance proximate the tissue treatment site; pairing the position information with the measured impedance; processing the paired position information and the measured impedance into a computer readable signal; graphically displaying the paired information; and modifying the operation of the ablation element based at least in part on the paired information.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1b is back view of a part of the medical system in FIG. 1a;

FIG. 6 is a front view of another exemplary medical device used in conjunction with the method shown in FIG. 4;

FIG. 7 is a perspective view of yet another exemplary medical device used in conjunction with the method shown in FIG. 4;

DETAILED DESCRIPTION OF THE INVENTION

Figure 1A:
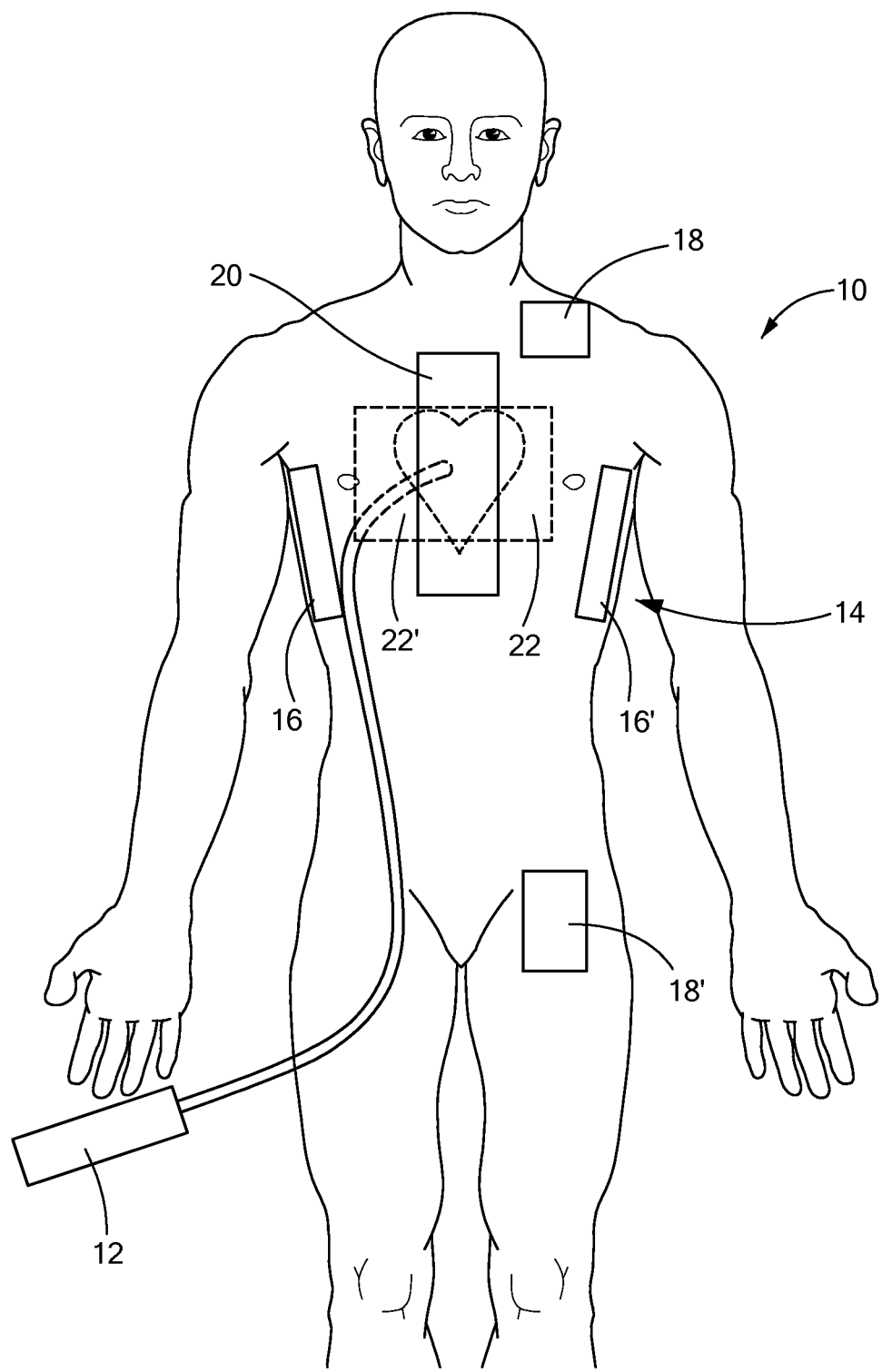
FIG. 1a is a front view of an embodiment of a medical system constructed in accordance with the principles of the present invention.
Figure 1B:
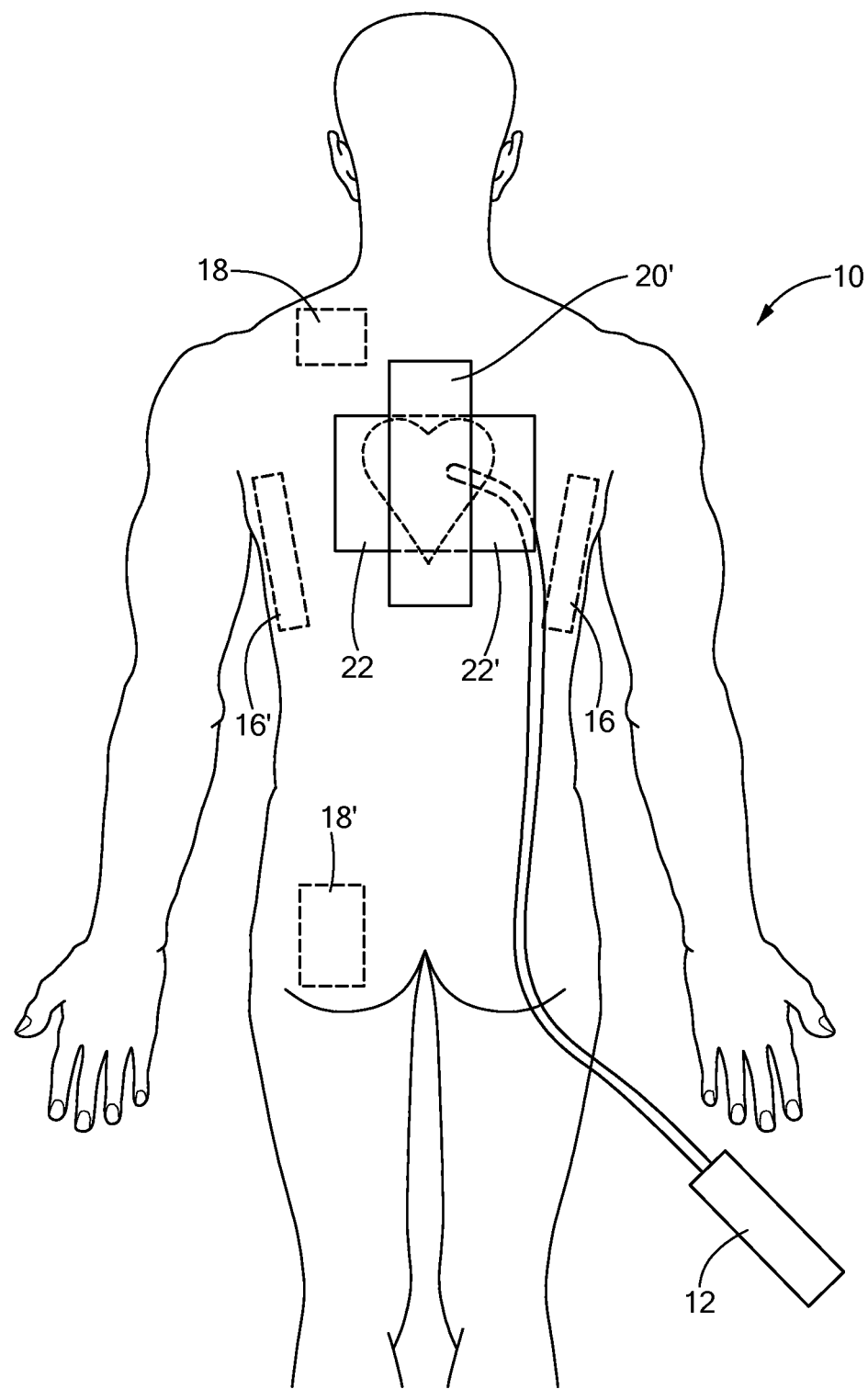

The present invention provides systems and methods of use thereof for pairing positional information of a medical device within a patient with device-based operational or physiological information for use during a medical procedure. In particular, device-originating measurements and information can be paired with device positioning information to provide a graphical or visual output that includes both device position relative to the anatomy and physiology of the patient, as well as location specific measurements and properties overlayed or otherwise included for the physician's reference during a medical procedure. Referring now to the drawings in which like reference designators refer to like elements, there is shown in FIGS. 1a and 1b, front and back views of an exemplary medical system pairing positional information with device-based operational or physiological information and designated generally as "10."

The system 10 generally includes a medical device 12, such as a cryogenic or radio-frequency ("RF") ablation catheter and the like. The medical device 12 generally includes an elongate body with a treatment portion having one or more energy transfer elements at a distal end portion. The medical device 12 may be adapted for percutaneous or surgical insertion into the body, and in particular, into the cardiothoracic region of a patient. The system 10 further includes one or more surface electrodes 14 positionable about the exterior of the patient (such as on the skin, for example) that include impedance measurement capabilities or other features allowing the detection, receipt, and/or transmission of an electrical signal. Each surface electrode 14 may have an adhesive surface that is removably affixable to the skin, or each surface electrode 14 may be implanted under the skin. Optionally, conductive gel (not shown) may be applied to the skin subjacent to the surface electrode 14 to increase the conductivity or adhesiveness between surface electrodes 14 and the body of the patient.

In an exemplary embodiment, three pairs of surface electrodes 14 are adhered to the skin to provide three-dimensional position information in x, y, and z planes. For example, as shown in FIGS. 1a and 1b, surface electrodes 14 include surface electrodes 16 and 16' adhered to the right and left sides of the chest of the patient; surface electrodes 18 and 18' adhered to portions of the neck and thigh respectively; and surface electrodes 20 and 20' adhered to the chest and back respectively.

Additional surface electrodes 14 may be adhered to the skin of the patient as desired in any number of desired locations to provide additional positional information, precision, and/or accuracy, as described more below. The surface electrodes 14 may be connected to a power supply, such as a generator, a display 32 (FIG. 2) and/or other signal processing components (such as those disclosed in U.S. Pat. Nos. 5,697,377 and 5,983,126, the entirety of each of which is incorporated herein by reference) to process and display information regarding or relating to the electrical signals sensed by the surface electrodes 14.

Continuing to refer to FIG. 1b, in addition to surface electrodes 14, one or more reference electrodes 22 may be adhered to the skin of the patient in a similar fashion to that of the surface electrodes 14, or alternatively be disposed within the body of the patient, for example, at a location proximate or within the heart. For example, as shown in FIG. 1b reference electrodes 22 and 22' may be adhered to the back of the patient on opposite sides of surface electrode 20'. Reference electrodes 22 and 22' may be grounded such that they are operable to receive RF energy during an RF energy treatment provide by the medical device 12. Alternatively, reference electrodes 22 and 22' may include a grounded, non-adhesive plate positionable beneath the patient. Additionally, any or all of the surface electrodes 14 may be selectively operable as ground electrodes during, for example, delivery of RF energy in a unipolar mode, as discussed in more detail below.

The medical device 12 of the system 10 may include one or more ablation elements 24 coupled to a distal assembly 26 of the medical device 12. The distal assembly 26 of the medical device 12 is the treatment portion of the medical device 12 navigated towards and placed proximate to the target tissue to be treated. For example, exemplary medical devices 12 having ablation elements 24 are shown in FIGS. 5-8a and are discussed in more detail below. The ablation elements 24 may include, for example, RF electrodes, cryogenic chambers, ultrasound emitters, laser emitting diodes, and other ablative elements known in the art.

The medical device 12 may be used in conjunction with the surface electrodes to provide positioning information of the device within the patient. In particular, in addition to the ablation elements 24, each of these exemplary medical devices 12 shown in FIGS. 5-8a may include one or more electrodes 28 coupled to the distal assembly 26 operable to transmit electrical energy and/or measure impedance activity between a pair of the surface electrodes 14. Based on this electrical or impedance activity, the position of the medical device 12 may be tracked and monitored as it is advanced towards the target tissue and as it navigates from one treatment site to the next. For example, electrical potential localization (EPL) may used to localize or triangulate the position of the electrodes 28 in three-dimensional space, allowing the surgeon to accurately determine the position of the medical device 12 with respect to surrounding tissues.

Localization and triangulation of the electrodes 28 may be obtained by measuring and recording the electric potential or impedance activity between two or more of the surface electrodes 14 and between one or more of the surface electrodes 14 and the electrodes 28, in sequence or simultaneously. For example, an electric potential, which may be orthogonal, may be applied across surface electrodes 16, 16', 18, 18', 20, and 20' in sequence or simultaneously and sensed and measured by electrodes 28. From this measurement of electric potential or impedance, the position of the medical device 12 in x, y, and z planes may be extrapolated based on the known or calculated interelectrode distances between the surface electrodes 14. Any of the electrodes 28 may be further selectively operable to extrapolate the position of a portion of the medical device 12 for increased accuracy. For example, the embodiments of exemplary medical devices 12 shown in FIGS. 5-8a each may have one or more of electrodes 28 included on their respective distal assemblies 26. Should the surgeon desire to determine the position of a particular portion of the medical device 12, a particular electrode 28 may be activated to determine that position.

The frequency of the electric fields generated and applied to the surface electrodes 14 may be different between two surface electrode 14 pairs to minimize interference and to isolate each potential or impedance measurement. For example, the current may be applied between surface electrodes 16 and 16' at a frequency of 30 kHz and between surface electrodes 18 and 18' at a frequency of 40 kHz. The duration at which each electric field is applied may be constant or variable depending on the desired measurement. For example, if the "x" position of the medical device 12 is the desired measurement during a treatment, the voltage potential applied to surface electrodes 14 that measure potential or impedance along the "x" position of the medical device may be applied for a longer duration of time than the electrodes that measure potential or impedance in the "y" or "z" positions.

In addition to localization information, the system 10 includes physiological assessment information or device operating parameters provided by the medical device 12. In particular, the ablation elements 24 and/or electrodes 28 may be operable to obtain physiological assessment information, such as impedance and temperature measurements, tissue contact assessment information, fluid flow rates, pressures, electrical activity, etc. The distal assembly 26 may have a plurality of electrodes 28 or other sensors facilitating the monitoring, measuring, and or recordation of these exemplary parameters.

Figure 2:
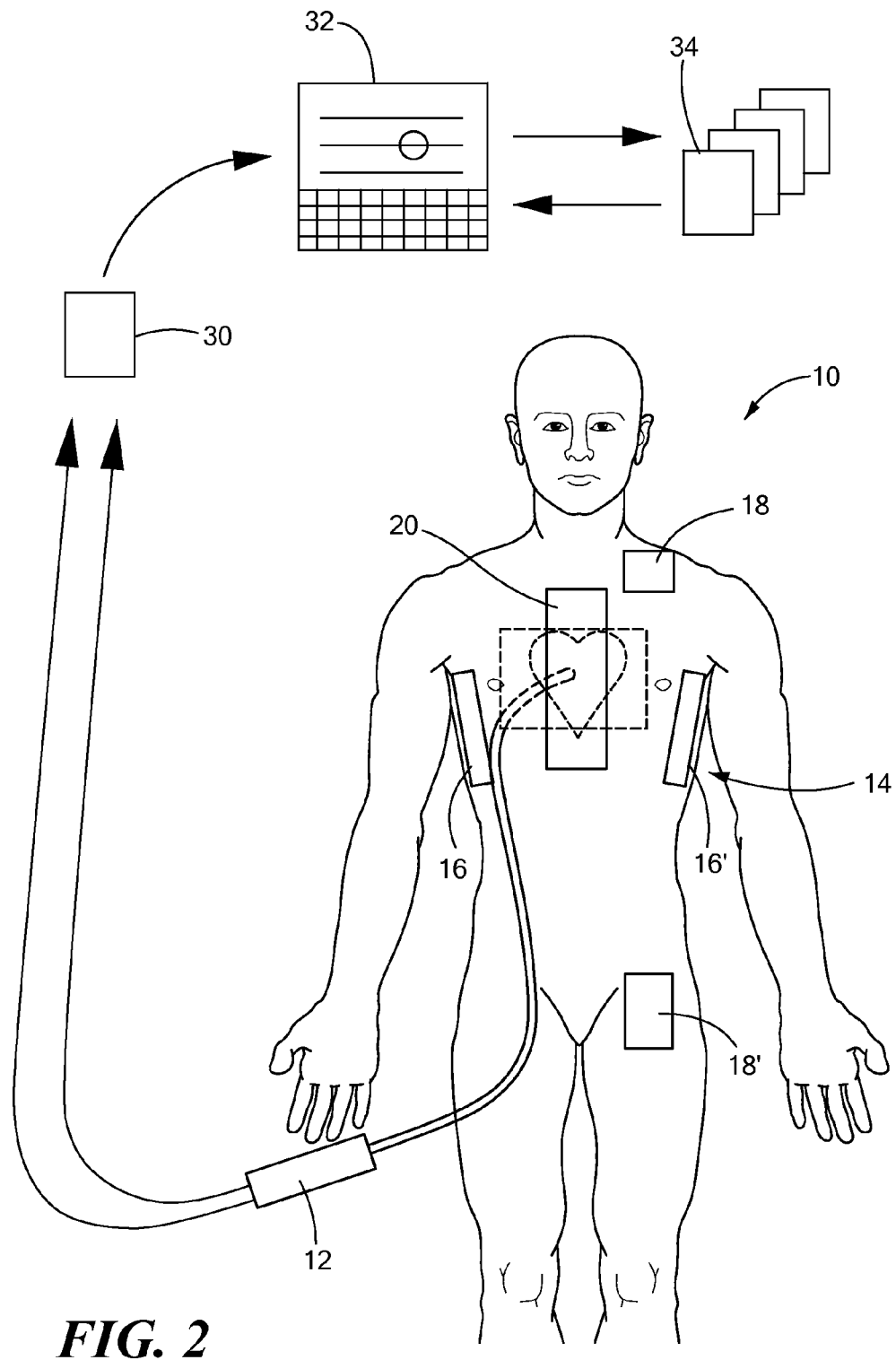
FIG. 2 is another schematic of a medical system constructed in accordance with the principles of the present invention.

Referring now to FIG. 2, the system 10 may further includes a processor 30 to process positional information and the physiological assessment/device operational information. For example, location information obtained from the surface electrodes 14 and physiological assessment information obtained from the medical device 12 may each be relayed through one or more wires to the processor 30. The processor operates to multiplex or pair the measured position and physiological assessment information into one or more computer readable signals. The computer readable signal may then be displayed on a display 32 where a visual image of the combined position and physiological data may be shown. The processor 30 and the display 32 may further be in communication with a database 34 that stores patient statistics, treatment history, or historic position and physiological assessment information. For example, real-time position and physiological information may be paired with or displayed with historic information on the display 32 as an easy-to-read single source of treatment information before, during, or after a medical procedure at a specific location within the patient's anatomy. As such, as the surgeon moves the medical device 12 to a different location, he can monitor both the physiological assessment information and position information on a single display for that specific location.

Figure 3:
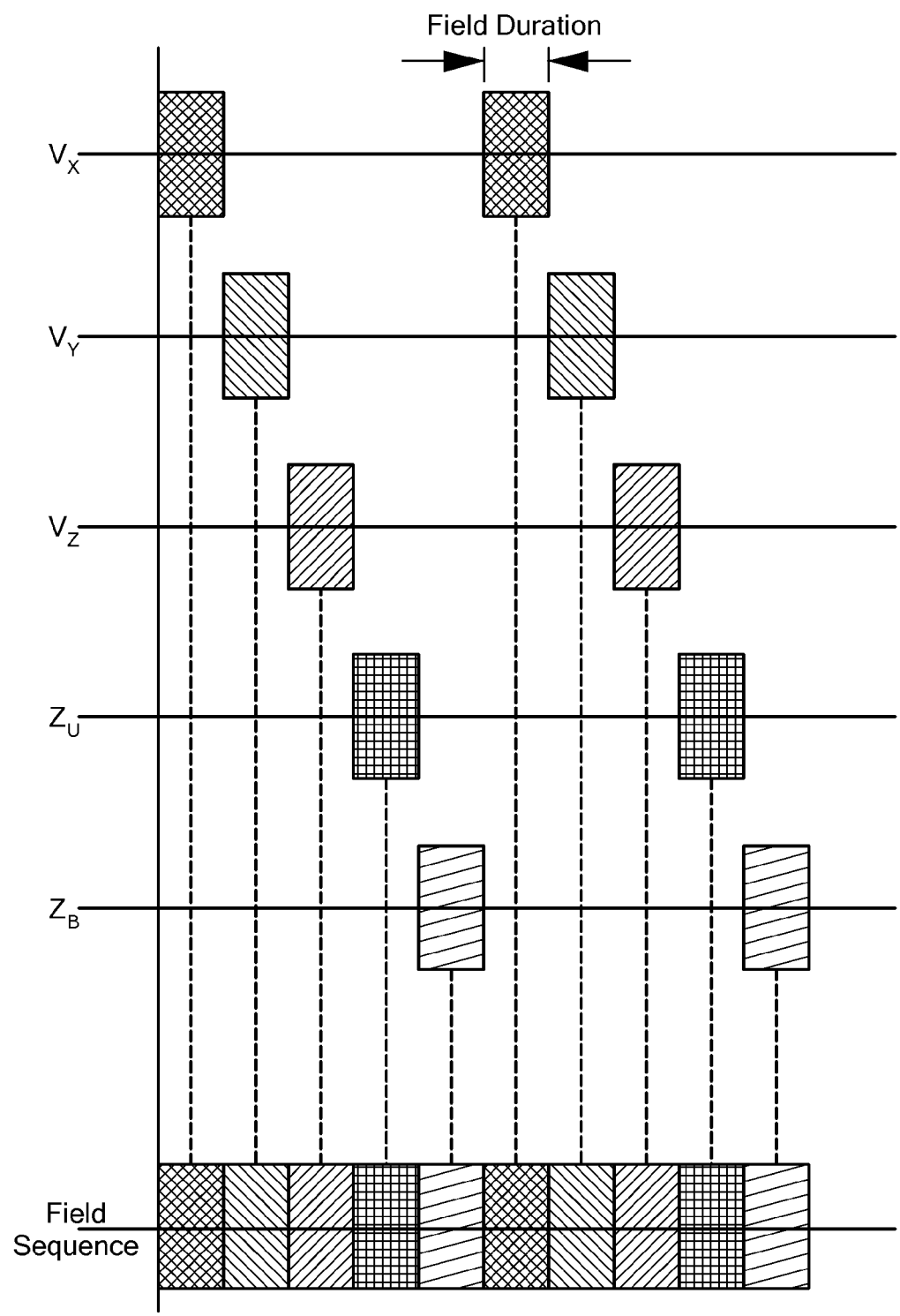
FIG. 3 is a graph showing the sequence and duration of applying electrical current across various electrodes of the medical systems of FIGS. 1a-2.

The position and physiological assessment information may be paired sequentially or simultaneously. For example, a process of obtaining real-time position and device-originated information is shown in FIG. 3. Voltage potentials "Vx," "Vy", and "Vz" and impedance measurements "Zu" and "Zb" are each processed and recorded in sequence and for the same time duration. Vx represents the measurement of the voltage potential applied between surface electrodes 16 and 16' when a current is applied; Vy represents the voltage potential applied between surface electrodes 18 and 18' when a current is applied; Vz represents the voltage potential applied between surface electrodes 20 and 20' when a current is applied; Zu represents the impedance measured between electrode 28 or ablation elements 24 and either reference electrodes 22 or 22' when the medical device 12 is operable to deliver unipolar RF energy; and Zb represents the impedance measured between two or more electrodes 28 or ablation elements 24 disposed on the medical device 12, for example, during bipolar transmission of RF energy. Some or all of these measurements may be recorded in any sequence and for any time duration. For example, if a measurement of the x, y position of the medical device 12 is desired, Vx and Vy may be recorded and multiplexed with or without a Zu and/or Zb measurement.

Alternatively, any or all of Vx, Vy, Vz, Zu, and Zb may be impedance or electric potential measurements, and may be measured from constant, intermittent, or phased current and may be obtained simultaneously. For example, when providing both unipolar and bipolar RF energy to the treatment site, physiological assessment information, such as impedance measurements Zu and Zb, temperature, or contact assessment, can be made over a pre-determined period of time. For example, Vx, Vy, and Vz can be continuously measured as medical device 12 is advanced and is navigated towards the target tissue. Upon reaching the target tissue site, bipolar and/or unipolar RF energy may be transmitted to the target tissue, in combination or in sequence. As treatment energy is transmitted to the target tissue, the measured impedance may change. Any changes can be measured by Zu (unipolar) and Zb (biopolar) and may be multiplexed or paired by, for example, the processor 30 (FIG. 2), with Vx, Vy, and Vz information into one or more computer readable signals that provide both position and physiological assessment information. The processed position and physiological assessment information can then be visually displayed on display 32 during a procedure to provide overall treatment assessment information. Optionally, the medical device 12 may include additional electrodes or sensors that may act in combination or may be multiplexed with Vx, Vy, Vz, Zu, and/or Zb to yield more than position or impedance information. For example, the unipolar or bipolar RF ablation elements 24 may be operable to both sense impedance and ablate tissue. Additionally, temperature information obtained from thermocouples coupled to medical device 12 can be multiplexed with the positional, potential, or impedance information obtained from Vx, Vy, Vz, Zu, and/or Zb to provide information about the efficacy of the treatment.

The system 10 can further be adjusted and calibrated to compensate for variations in measurements owing to, for example, respiration or movement of the patient. For example, because the patient is breathing during treatment, Vx, Vy, Vz, Zu, and Zb measurements may vary during respirations. The measured impedance may decrease upon exhalation and increase upon inhalation. These variations can be measured and off-set by calibrating the multiplexed signal during an initial assessment period before treatment. Alternatively, a filter can be applied to any of the measured Vx, Vy, Vz, Zu, and Zb signals to eliminate noise and collateral effects on the measured potential or impedance.

Figure 4:
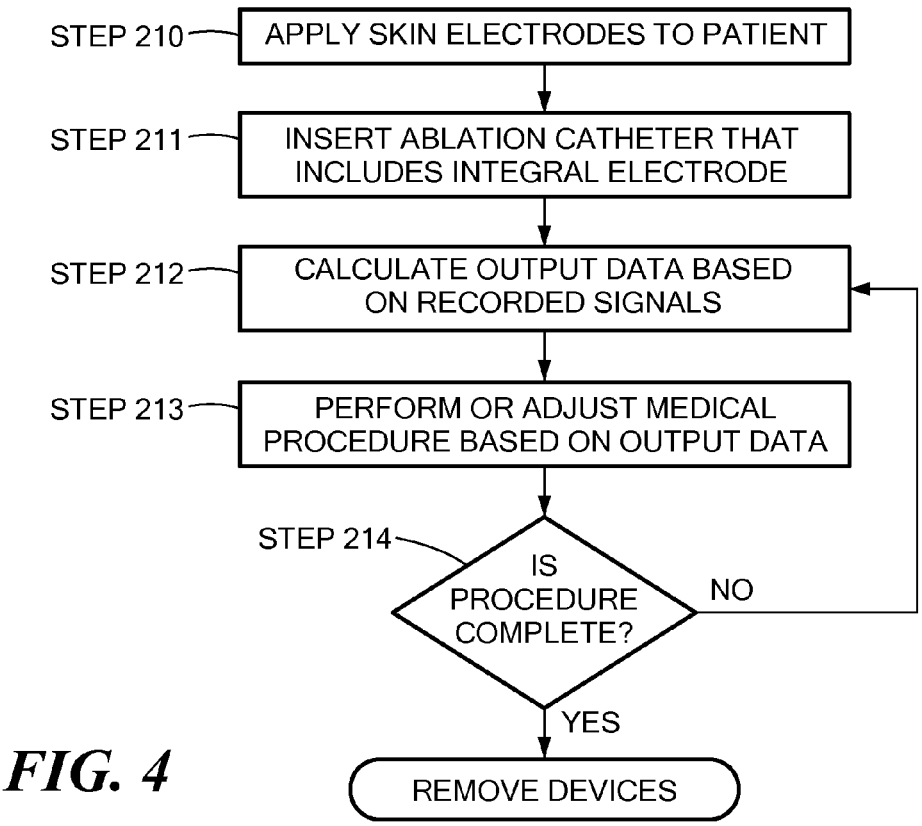
FIG. 4 is a flow chart of a medical method of use of the medical systems of FIGS. 1a-2 in accordance with the principles of the present invention.

Referring now to FIG. 4, an exemplary method of treatment using the system 10 discussed above is shown. Initially, the surface electrodes 14 and reference electrodes 22 are applied to the skin either while the patient is in a supine position or while standing up, and an electric potential is applied to the surface electrodes 14 (Step 210). Next, a medical device 12, for example, those disclosed in FIGS. 5-8a, is advanced through the vasculature towards the target tissue (percutaneously or surgically, for example) (Step 211). For example, as shown in FIG. 9, in performing a procedure to correct atrial fibrillation, the medical device 12 may be inserted into the venous system and navigated into the patient's heart, through the inter-atrial septum, and the into the left atrium of the patient where the target tissue resides. As the medical device 12 is navigated through the vasculature, voltage potential and/or impedance measurements are measured and recorded, as discussed above, by one or more pairs of surface electrodes 14 and electrodes 28 and its position may be visually displayed for the operator or physician. When the medical device 12 reaches it its target site, a medical procedure, such as RF ablation, cryoablation, or the like may be initiated. During this procedure, various operating parameters such as temperature, tissue contact assessment, tissue impedance measurements, flow rates of fluids through the device, pressure in or around the catheter, etc. may be monitored or provided by the medical device by one or more sensors. The positional measurement data is then multiplexed, paired, or otherwise combined with the operational, device-based information, and may include, for example, the impedance data measured and recorded between one or more electrodes 28 or ablation elements 14 (bipolar) and between one or more electrodes 28 and reference electrodes 22 and/or 22' (unipolar) (Step 212). This paired data may then be processed by processor 30 and displayed to identify the operational parameters (such as temperature, tissue assessment, etc.) at specific locations (as provided by the surface electrodes) for the medical device. This information may be used to determine or otherwise asses the efficacy of the treatment or the status of the medical device.

Based on the data retrieved and assessed in Step 212 and displayed on display 32, the medical procedure may then be continued at a different treatment site or adjusted (Step 213). For example, energy delivery may be initiated, continued, or terminated based on the operational information provided by the device in conjunction with the position of the device. For example, a target tissue impedance level of an ablation site can be predetermined before treatment and treatment may be stopped should that target tissue impedance level be reached. In particular, if the target tissue is frozen or burned, the associated changes in the electrophysiology of the target tissue can be detected by the impedance measurements proximate the treated tissue. Further, by pairing this information with the positional information, the physician can visually identify where these impedance levels are being recorded and adjust the treatment delivery and/or positioning based on such information.

In embodiments of the present invention where the medical devices 12 is an RF ablation catheter, Zu and/or Zb, may be measured proximate the pulmonary vein ("PV") antrum or the Fossa-Ovalis. For example, RF energy may be delivered to the PV antrum, but care in positioning the medical device 12 is typically advised to avoid causing a pulmonary vein stenosis. Impedance measurements Zu and/or Zb may be measured in combination with Vx, Vy, and Vz and the paired data may be correlated to determine the accuracy of RF delivery at the PV antrum. For example, a higher impedance indicates that the distal assembly 26 of the medical device 12 may be positioned within the pulmonary vein and a lower impedance indicates the medical device 12 may be positioned in the atrium. Alternatively, should the target tissue be the Fossa-Ovalis, one or more electrodes 28 may be positioned proximate a septal penetrator coupled to the distal assembly 26 of the medical device 12, and Zu and/or Zb in combination with Vx, Vy, and Vz, may be measured to determine when contact is made with the Fossa-Ovalis. For example, an impedance measurement indicative of a lack of muscle contractions may further indicate that the Fossa-Ovalis has been contacted.

The completeness or efficacy of any or all of the above procedures, or any other procedure using the above method, may be based in part or fully on any or all of Vx, Vy, Vz, Zu, and Zb measurements (Step 214) or historic information recorded and measured previously from the patient, or a combination of each. For example, in an embodiment where a cryogenic procedure is performed, if Zu and/or Zb reach a predetermine value, or if the time rate of change of Zu and/or Zb reaches zero, the target tissue may be frozen and the treatment may be terminated. Alternatively, if the treatment is not complete, Steps 212 and 213 may be repeated and/or modified based on real-time or historic information until the desired measurements are reached. For example, if measurements of Vx, Vy, and Vz, determine that the medical device 12 is not in the correct position for treatment, Steps 212 and 213 can be repeated until a either the desired target area is treated or a desired tissue condition is achieved.

Based on the measured data obtained from Vx, Vy, Vz, Zu, Zb, and/or other sensor measurements from medical device 12, it is contemplated that various tissue or treatment assessment information may be measured, calculated, or correlated from the processed paired data. For example, lesion quality data, tissue contact data, tissue anatomy data, respiration data, electrogram amplitude and fractionation data, local activation timing data, fibrillatory wave (F-wave) cycle length data, dominant F-wave frequency data, action potential duration data (APD), refractoriness data, and/or combinations of the above may all be calculated. Any of the above data may be measured during Step 212 to determine if treatment needs to be modified in Step 213. For example, the delivery ratio of unipolar to bipolar energy may be modified based on any of the above calculated data.

In another example, measurement of APD data may be paired or multiplexed with data measured from a monophasic action potential (MAP) sensor coupled to the medical device 12 and positioned proximate the treatment site. For example, MAP and APD may be recorded sequentially or simultaneously with any of the above data, wherein the MAP sensor may record action potential signals from the surrounding tissue in the range of, for example, 0.05 Hz to 500 Hz, and increase the calculation time for APD data acquisition. From this data, a dispersion assessment of action potential durations may be calculated. The MAP and APD data may further be correlated with Vx, Vy, Vz, Zu, Zb, and/or any of the above data to provide endocardial surface information which may be visualized by the surgeon during a treatment. Based on MAP, APD, and other calculated data discussed above, thresholds may be established above or below which energy is delivered to a treatment site.

Optionally, patient imaging, such as MRI, CT, X-ray, ultrasound, and the like, may be performed before and/or after the above method is completed to provide anatomical data of the patient to assess the efficacy of the treatment. For example, in an RF ablation treatment, imaging of the target issue may be performed before and after treatment to determine the extent of the ablation. If the desired result is not achieved, Steps 211-214 may be repeated.

Figure 5:
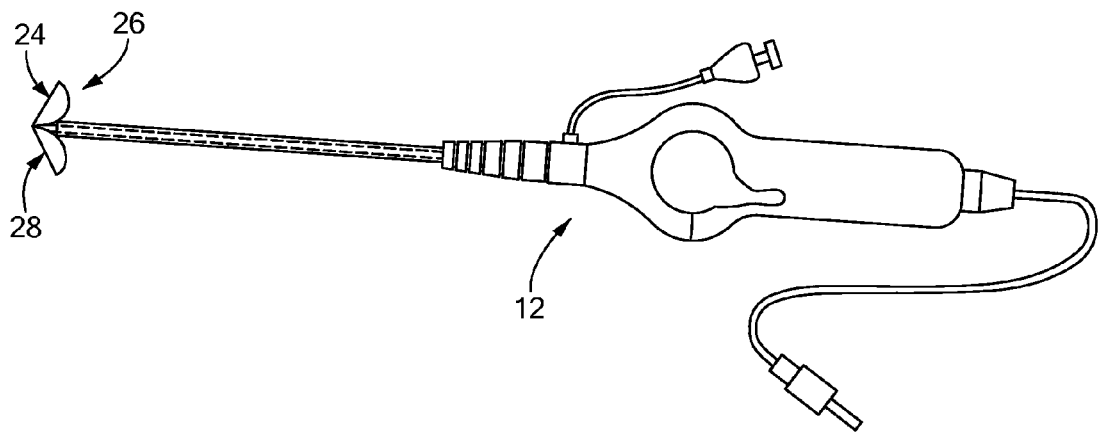
FIG. 5 is a side view of an exemplary medical device used in conjunction with the method shown in FIG. 4.

Referring now to FIG. 5, an exemplary medical device 12 is shown that may be used with the above system 10 and method. The medical device 12 is an RF ablation catheter having a distal assembly 26 including ablation elements 24 in communication with a generator and one or more electrodes 28. In the illustrated embodiment, the distal assembly 26 of the medical device 12 includes a carrier assembly having three carrier arms including ablation elements 24 as described in U.S. Pat. No. 7,468,062, the entirety of which is incorporated herein by reference. The ablation elements 24 and/or electrodes 28 may be operated with surface electrodes 14 (not shown) to measure Vx, Vy, Vz, Zu, Zb and/or any of measurements discussed above, and deliver unipolar and bipolar RF energy to tissue, in particular the septal wall, in accordance with the method described above. Optionally, one or more MAP sensors or an electromagnetic localization element (ELE) may be included on medical device 12 and may provide measurements in accordance with the method described above.

Referring now to FIG. 6, another exemplary medical device 12 is shown that may be used with the above system 10 and method. The medical device 12 is an RF ablation catheter having a distal assembly 26 including elements 24 in communication with a generator and one or more electrodes 28. In the illustrated embodiment, the distal assembly 26 of the medical device 12 includes a carrier assembly having four carrier arms including ablation elements 24 as described in U.S. Pat. No. 7,429,261 the entirety of which is incorporated herein by reference. The ablation elements 24 and/or electrodes 28 may be operated with surface electrodes 14 (not shown) to measure Vx, Vy, Vz, Zu, Zb and/or any of the measurements discussed above, and deliver unipolar and bipolar RF energy to tissue, in particular the atrial wall, in accordance with the method described above. Optionally, one or more MAP sensors or an ELE may be included on medical device 12 and may be measured in accordance with the method described above.

Referring now to FIG. 7, yet another exemplary medical device 12 is shown that may be used with the above system 10 and method. The medical device 12 is an RF ablation catheter having a distal assembly 26 including ablation elements 24 in communication with a generator and one or more electrodes 28. In the illustrated embodiment, the distal assembly 26 of the medical device 12 includes a flexible and deflectable helical wire having ablation elements 24 as described in U.S. application Ser. No. 11/471,467 the entirety of which is incorporated herein by reference. The ablation elements 24 and/or electrodes 28 may be operated with surface electrodes 14 (not shown) to measure Vx, Vy, Vz, Zu, Zb and/or any of the measurements discussed above, and deliver unipolar and bipolar RF energy to tissue, in particular the pulmonary vein, in accordance with the method described above. Optionally, one or more MAP sensors or an ELE may be included on medical device 12 and may be measured in accordance with the method described above.

Figure 8:
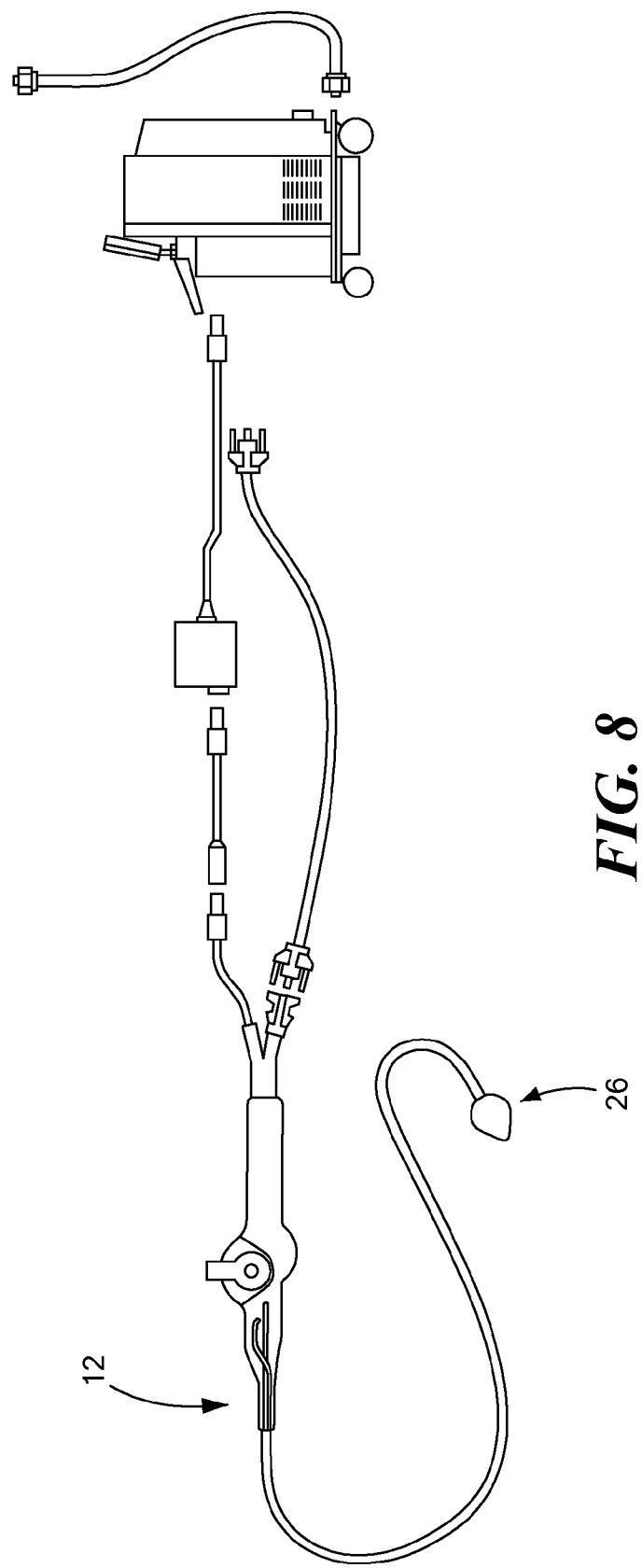
FIG. 8 is a side view of an exemplary medical device used in conjunction with the method shown in FIG. 4.
Figure 8A:
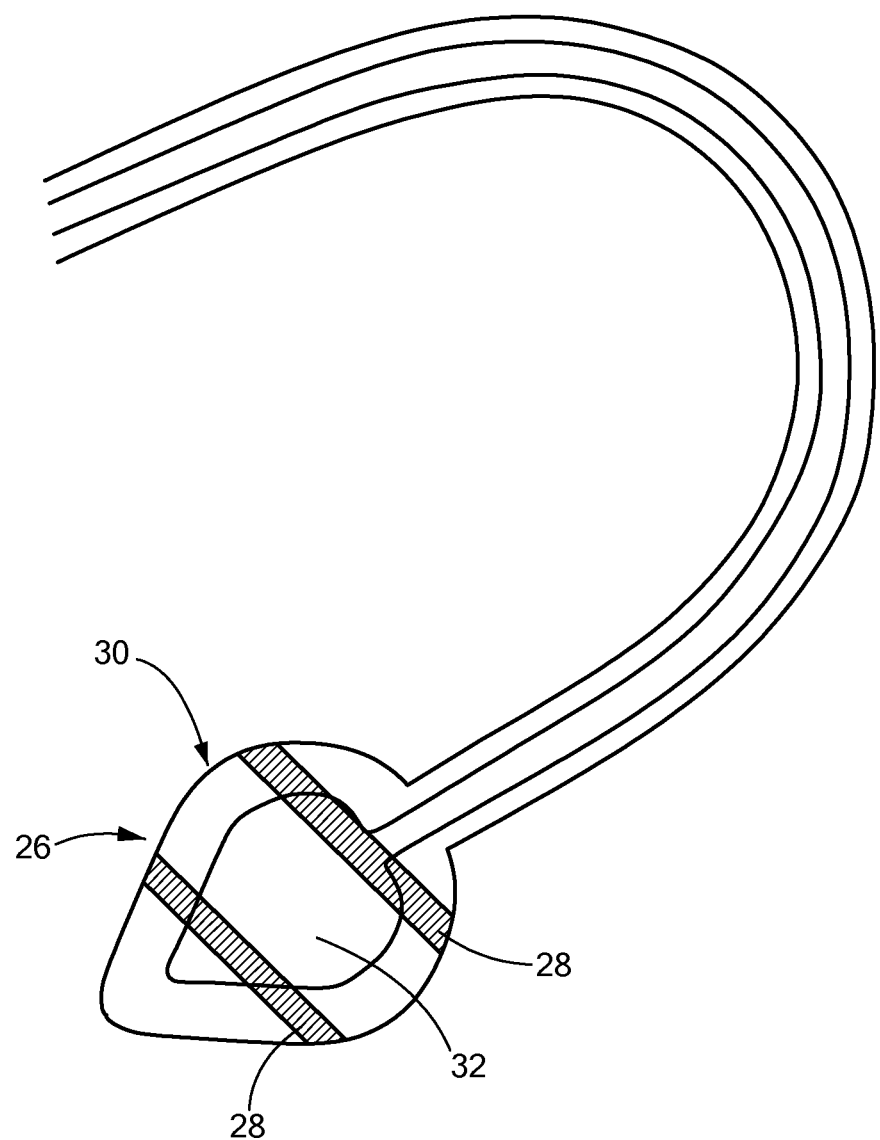
FIG. 8a shows the distal end of the medical device shown in FIG. 8.
Figure 9:
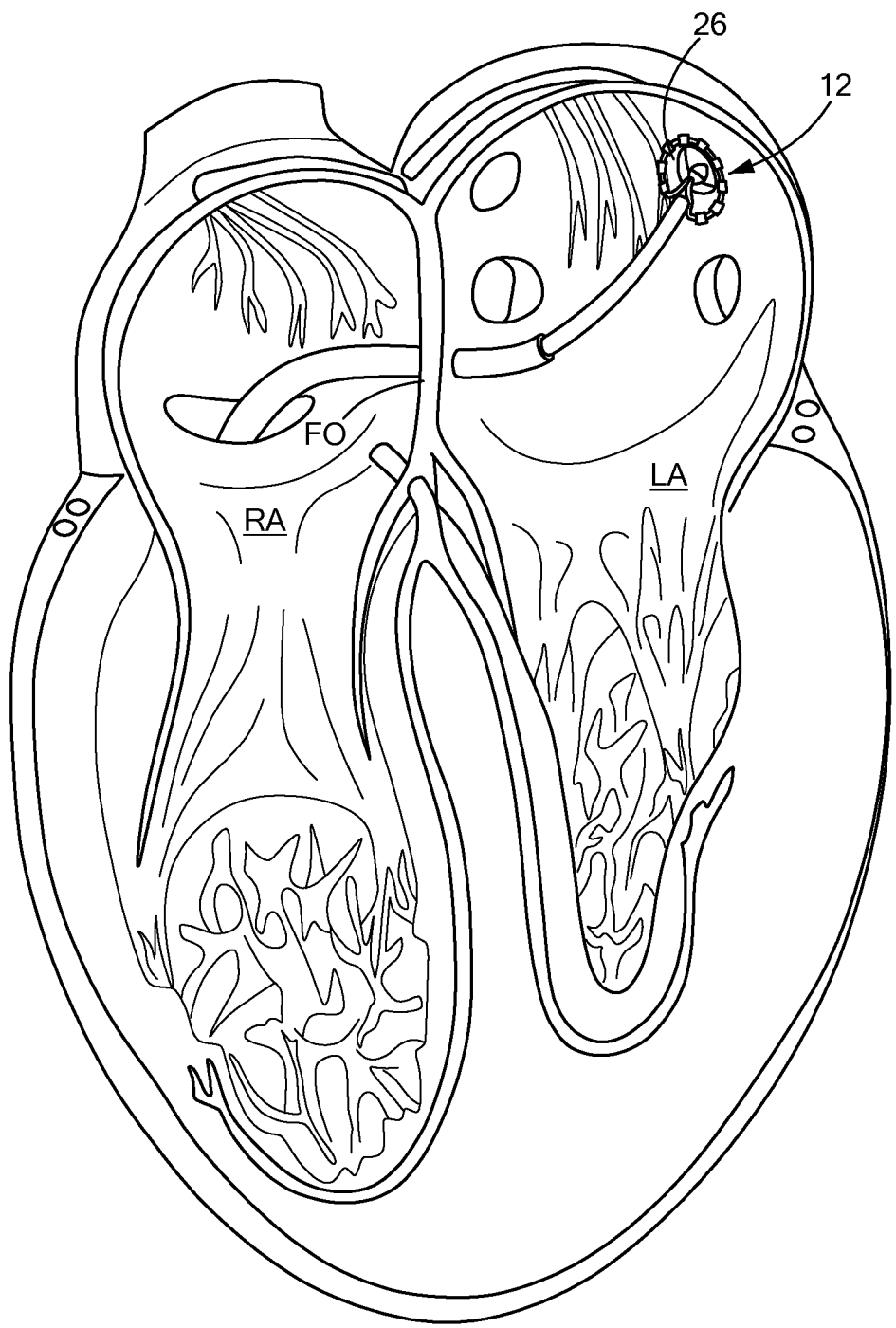
FIG. 9 shows the medical device shown in FIG. 7 proximate a tissue region to be treated in the heart.

Referring now to FIGS. 8 and 8a, yet another exemplary medical device 12 is shown that may be used with the above system 10 and method. Medical device 12 is a cryogenic catheter including an elongate body defining a proximal and distal end and one or more fluid pathways there through. The cryogenic catheter may include at least one expandable member 36 defining a cryogenic chamber 38 coupled to the distal assembly 26 of the device. The expandable member 36 is further in fluid communication with a cryogenic fluid source. One or more electrodes 28 may be coupled to the catheter at the distal assembly 26. For example, as shown in FIG. 7a, the expandable element may be disposed between two or more electrodes 28 or may include one or more electrodes 28 coupled to the expandable member's 36 surface. Any of the electrodes 28 may cooperate to measure Zu, Zb, and/or Vx, Vy, or Vz. Optionally, one or more leak detectors or pressure sensors may be positioned about the distal assembly 26 of the catheter and the measured information from these components may be paired or multiplexed with any of the above measurements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system comprising:
a medical device having a distal assembly including at least one electrode and at least one treatment element, the medical device obtaining information regarding impedance;
a plurality of surface electrodes affixable to a skin of a patient, wherein the surface electrodes are in electrical communication with the distal assembly to obtain position information of the medical device;
an energy generator in electrical communication with the distal assembly and the plurality of surface electrodes, the generator being configured to deliver ablation energy to the treatment element in unipolar mode and bipolar mode simultaneously;
a processor, the processor being configured to obtain the information regarding impedance from the medical device and the position information of the medical device from the plurality of surface electrodes simultaneously when ablation energy is being delivered to the treatment element, the processor pairing the position information and the information regarding impedance.

2. The medical system of claim 1, further comprising a reference electrode affixable to the skin of the patient in electrical communication with the distal assembly.

3. The medical system of claim 2, wherein the treatment element is a radiofrequency ablation element.

4. The medical system of claim 1, wherein the plurality of electrodes includes at least three pairs of surface electrodes.

5. The medical system of claim 4, wherein the at least three pairs of surface electrodes cooperate with the distal assembly to measure electric potential in three different planes.

* * * * *